United States Patent [19]

Burkhart

[11] Patent Number: 5,217,471
[45] Date of Patent: Jun. 8, 1993

[54] ENDOSCOPIC SUTURE KNOTTING INSTRUMENT

[76] Inventor: Stephen S. Burkhart, 201 Village Cir., San Antonio, Tex. 78232

[21] Appl. No.: 708,514

[22] Filed: May 30, 1991

[51] Int. Cl.$^5$ .............................................. A61B 17/00
[52] U.S. Cl. .................................. 606/148; 606/139; 606/205
[58] Field of Search .................... 606/148, 144, 139

[56] References Cited

U.S. PATENT DOCUMENTS

| | | | |
|---|---|---|---|
| 2,455,833 | 12/1948 | Trombetta | 606/139 |
| 4,935,027 | 6/1990 | Yoon | 606/148 X |
| 5,037,433 | 8/1991 | Wilk et al. | 606/139 |
| 5,084,058 | 1/1992 | Li | 606/148 |

*Primary Examiner*—Stephen C. Pellegrino
*Assistant Examiner*—Jeffrey A. Schmidt
*Attorney, Agent, or Firm*—Gunn Lee & Miller

[57] ABSTRACT

A method and apparatus for tightening of knots formed at a remote location in the body through the endoscopic surgical technique utilizing a knot pusher (10) having a cylindrical end face with diametrically opposed suture guide notches (16) formed on such end face (14). The knot pusher (10) defines an elongated groove (12) for reception of the elongated body portion (22) of a knot clamping instrument (20). The application of a pulling force (T) to the knot after it has been positioned adjacent the body parts results in the knot being tightened by forces which are generally radial to the axis of the knot pusher (10). The knot clamping instrument (20) is utilized to secure a previously formed knot while a second knot is formed in the ends of the suture and moved into position by the knot pusher (10).

5 Claims, 2 Drawing Sheets

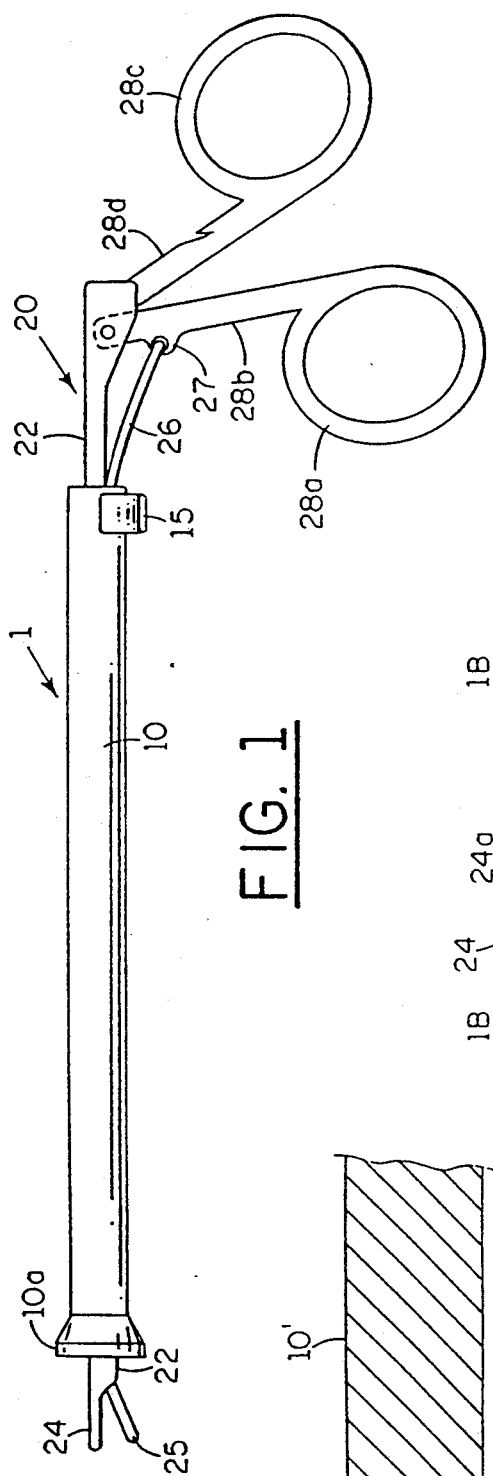
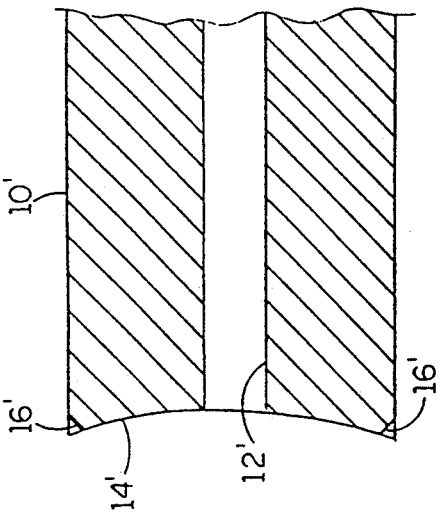
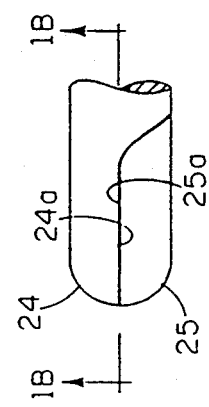
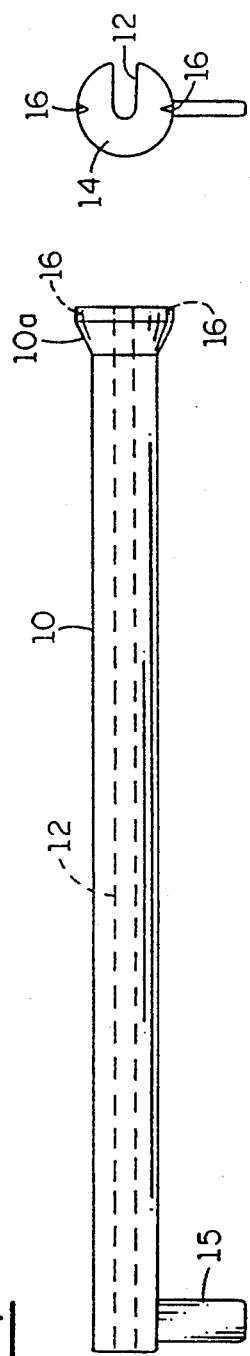
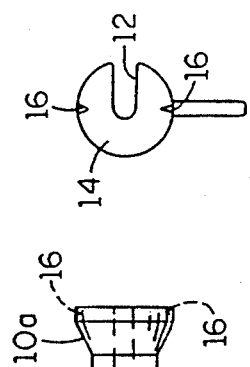

ENDOSCOPIC SUTURE KNOTTING INSTRUMENT

FIELD OF THE INVENTION

The present invention relates to suturing instruments and, more particularly, to instruments for endoscopic tying suture knots within a remote location within the body accessible by a small incision or a puncture wound.

SUMMARY OF THE PRIOR ART

Endoscopic surgery, which is used herein to encompass surgery on various parts of the body requiring only small incisions or puncture wounds for insertion of diagnostic and surgical instruments manipulated externally of the body, as well as surgery performed on joints, is preferable over open surgery to avoid the trauma associated with large incisions, as well as the hospitalization and prolonged recovery periods required with open surgery. Endoscopic surgery is therefore used whenever possible to achieve the same results as open surgery without the disadvantages thereof. Endoscopic techniques include internal viewing for diagnosis and identification of problems as well as surgical operations such as meniscus removal or repair, shaving of irregular, roughened patella and other surfaces, and articular surface smoothing. It may also be utilized to secure a severed tendon or muscle to a bone element.

Whatever type of surgery is accomplished endoscopically, there is involved the problem of tying knots in a suture used to secure body parts together at a remote location within the body. This problem has been addressed in the prior art,. See, for example, U.S. Pat. No. 4,890,615 to CASPARI et al. and the various prior art patents referred to in columns 1 and 2 of the CASPARI et al. patent. Instruments illustrative of the types used to "grab" debris or loose bodies during endoscopy are the 3370, 3371 Schlesinger Intervertebral Disk Rongeur with serrated jaws to facilitate removal of bone fragments from the from the lamina or facet (available from Zimmer, Inc., P. O. Box 708, Warsaw, Ind. 46580).

A common disadvantage of all of the aforementioned prior art instruments for internal knot tying is the fact that the knot tightening force is generally applied in a direction which is away from the surface of the body parts traversed by the suture being tied. This problem is particularly serious when braided sutures are utilized. Monofilament sutures will transfer a tightening force to a previously loosely tied knot when a second knot is formed and tightened, but the frictional drag of braided sutures prevents the effective application of tightening force to a previously tied knot. Much more effective knots can be applied to any type of suture if a tying force can be applied to the knot in a direction generally parallel to the surface of the body part being sutured. In other words, looking at the knot relative to the small puncture wound, the knot tying should preferably be accomplished by a tensile force exerted on the ends of the suture being tied in a direction roughly perpendicular to the axis of the knot-tying instrument, rather than by forces exerted in a direction generally parallel with the instrument. An instrument for effecting endoscopic knot tying in such a preferred manner has not heretofore been available.

SUMMARY OF THE INVENTION

The present invention is generally characterized as a suture knottying instrument assemblage for use in endoscopic surgery which is insertable into the body through a small opening or puncture wound and is operable by manipulation of elements of the knot tying instrument performed externally of the body.

The knot-tying instrument embodying this invention comprises an elongated generally cylindrical, knot pusher member which is freely insertable within an endoscopic opening or wound, or within an endoscopic access tube or cannula inserted in the wound. The knot pusher is of sufficient length to extend from the desired final location of the suture knot to be formed to a position well outside the body. The inner end face of the knot pusher is generally radial to the longitudinal axis of the knot pusher and is provided with diametrically opposed suture guides—either notches or channels—formed in the periphery of the end face through which the suture ends are passed as they extend outwardly from the area to be sutured to a point externally of the body where they may be grasped by the surgeon.

A knot of any desired configuration, but particularly a knot that is best tightened by the application of forces that are radial with respect to the axis of the puncture wound, is formed in the suture ends and such knot is pushed through the puncture wound or the access tube to a position adjacent to the body parts being sutured. The suture portions immediately adjacent to the knot will then extend in a direction generally radial to the longitudinal axis of the cylindrical knot pusher so that the application of a pulling force on the two external ends of the suture will be translated into a radially directed tightening force on the knot.

Successive knots can readily be applied in accordance with this invention through the utilization of a knot clamping tool which is of elongated, small diameter configuration so as to extend from the knot to be clamped to a point external to the body. More importantly, the thickness dimensions of the elongated body of the knot clamping instrument is small enough to permit the instrument to be inserted within a longitudinal groove defined in the sidewall of the elongated, cylindrical knot pusher. Thus, after a knot is originally formed and positioned by the cylindrical knot pusher, or by any similar instrument, the knot clamping instrument may be inserted in the longitudinal groove of the knot pusher and manipulated to bring clamping jaws formed on the inner ends of the knot clamper into engagement with the previously formed knot. The knot pusher may then be removed while the knot clamping instrument remains in position with the knot clamped by the jaws of the knot clamping instrument through a force applied by a scissor handle arrangement disposed on the outer end of the knot clamping instrument.

A second knot is then tied in the suture ends externally of the puncture wound and the knot pusher is reinserted into the wound, or the access tube, by slidably engaging the elongated body portion of the knot clamping instrument into the groove of the elongated, cylindrical knot pusher. The ends of the suture are disposed in the suture guide (notches or channels) formed in the end face of the cylindrical knot pusher, and the knot pusher is advanced into the wound or access tube while a restraining force is applied to the outer ends of the suture, resulting in the second knot being moved axially through the puncture wound to end up in a position adjacent the previously formed knot. Again, the application of a tensile force to the suture ends disposed outside the body will convert into a generally radially directed force on the second knot and tighten that knot into secure engagement with the first knot held in the clamping jaws of the knot clamping instrument. The clamping jaws of the knot clamping instrument can then be released and the knot clamping instrument and the cylindrical knot pusher concurrently removed from the wound or the access tube. If additional knots are required, the clamping tube can be shifted to clamp the newly formed knot and the aforedescribed knot tying operation repeated.

While not limited thereto, this invention finds particular utility in the endoscopic securement of a torn shoulder muscle, known as a rotator cuff, to the humerus bone of the shoulder. The knots to be tied will be immediately adjacent the rigid bone surface and the application of a tightening force to the knot in a direction generally parallel to the bone surface is highly desirable.

Although the invention has been described in connection with the preferred embodiment, it is not intended to limit the invention to a particular form set forth, but on the contrary, it is intended to cover such alternatives, modifications, and equivalents as may be included within the spirit and the scope of the invention as defined by the appended claims.

BRIEF DESCRIPTION OF DRAWINGS

FIG. 1 is a side elevational view of a complete suture knot tying instrument embodying this invention.

FIG. 1A is an enlarged scale elevational view of the knot clamping jaws employed in FIG. 1 with the jaws shown in their closed position.

FIG. 1B is a sectional view taken on the plane B—B of FIG. 1A.

FIG. 2 is a side elevational view of the knot pusher employed in FIG. 1.

FIG. 3 is an elevational view of the outer end of the knot pusher.

FIG. 4 is an elevational view of the inner end of the knot pusher.

FIG. 7 is an enlarged scale, partial sectional view of a preferred embodiment of the knot pusher.

DESCRIPTION OF PREFERRED EMBODIMENT

Figure 5:
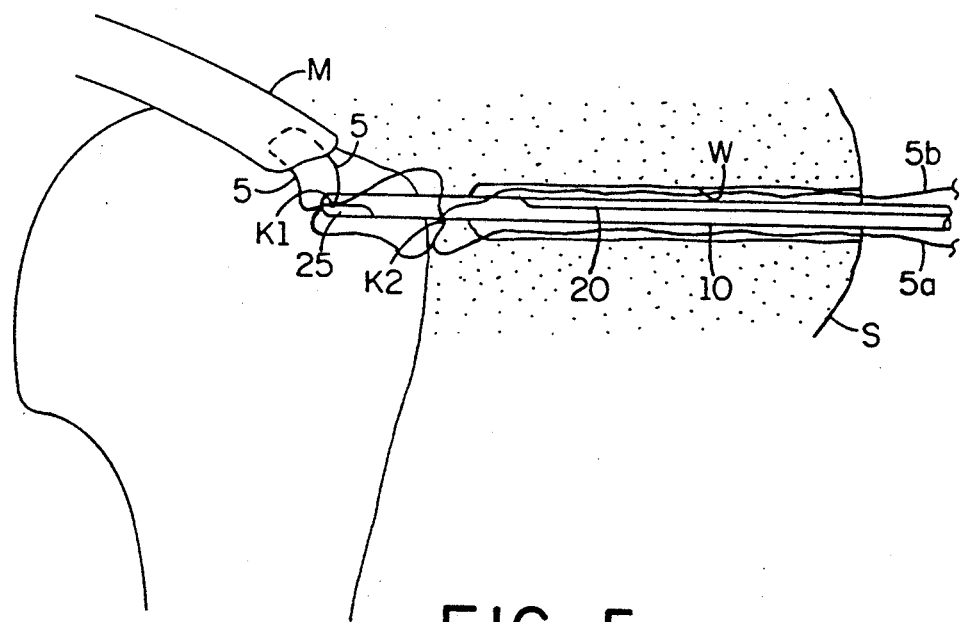
FIG. 5 is a schematic perspective view illustrating the employment of the knot tying instrument of FIG. 1 to effect the clamping of a first suture knot and the formation of a second suture knot.

Referring to FIGS. 1-4, an implement (1) for effecting the tying of the ends of a suture extending from remotely disposed body parts through a puncture-type wound comprises a knot pusher (10) of elongated, generally cylindrical configuration but having an elongated slot (12) extending through its entire length and thus making the cross-sectional appearance of the knot pusher resemble a generally "U" shape. Knot pusher (10) has an enlarged bulbous inner end portion (10a), as an alternative preferred embodiment, or has a non-bulbous end portion (10a) the same diameter as the body portion of knot pusher (10) (See, FIG. 7, (10'), the preferred embodiment being without the bulbous inner end portion); both embodiments having a radial inner end face (14). A pair of diametrically opposed suture guide notches (16) are provided on the periphery of radial end face (14). In the alternative, guide channels (16') may be provided for threading the suture ends therethrough (See, FIG. 7.) The diameter of bulbous portion (10a) may be up to a maximum that can be inserted into a puncture wound, for example, 15 mm. This provides maximum separation of suture guide notches (16) or channels ('16).

At the outer end of the knot pusher (10), a radially projecting handle (15) is rigidly secured to permit the surgeon using the device to readily shift the knot pusher (10) about its axis so as to align the suture guide notches (16) or channels (16') in a desired relationship with respect to the location of the suture (5) within the body. Handle (15) is preferably radially aligned with notches (16).

A knot clamping apparatus (20) is provided which is generally similar to the Schlesinger Intervertebral Disk Rongeur, except for the clamping jaws and other dimensional and design features, which are modified in accordance with this invention. Thus an elongated tubular body (22) is slidably insertable in the elongated notch (12) of the knot pusher (10) and has at its inner end a fixed jaw (24) with which a pivotally movable jaw (25) cooperates. The movable jaw (25) is shifted to and from a clamping position by an elongated link (26) which is pivotally secured by pin (27) to the movable shank portion (28b) of a scissor type handle (28a). A cooperating fixed scissor type handle (28c) has its shank portion (28d) rigidly secured to the outer end of the body portion (22) of suture knot clamping instrument (20).

It should be noted by reference to FIGS. 1A and 1B that the configurations of the fixed and movable jaws (24) and (25) are distinct from the jaws shown in the aforementioned U.S. Pat. No. 4,923,461 wherein the jaws are employed to effect the penetration of a needle into a body part as a preliminary to feeding a length of suture through tissue or muscle. The cooperating jaws (24) and (25) have planar surfaces (24a) and (25a) which are movable into abutment through the operation of the scissor handle (28a). It should also be noted, by reference to FIG. 1B, that the lateral corners of each jaw are rounded as indicated at (24b). This permits a suture knot which is being tightened across the inner ends of the jaws (24) and (25) to be moved closely adjacent to a knot held between such jaws. Lastly, it should be noted that in their knot clamping position, the jaws (24) and (25) are freely insertable within the recess (12), thus permitting end surface (14) of knot pusher (10) to be moved closely adjacent a knot clamped between jaws (24) and (25).

Figure 6:
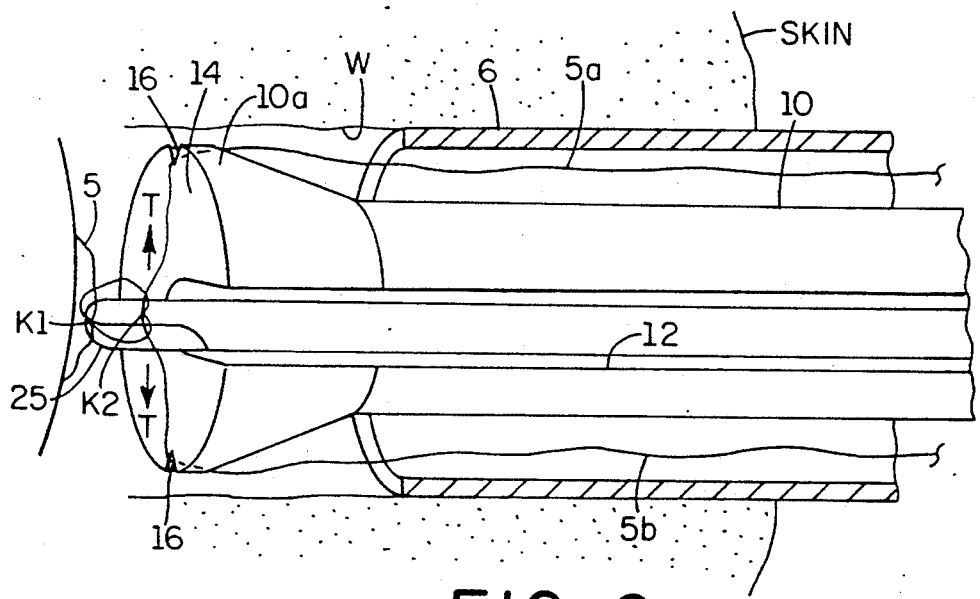
FIG. 6 is an enlarged scale view, partly in section, of a portion of FIG. 5 showing the knot pusher disposed in close proximity to the first suture knot secured by the knot clamping instrument.

The operation of the knot tying instrument embodying this invention will become readily apparent to those skilled in the art by reference to FIG. 5. While not limited thereto, the specific application of the knot tying instrument embodying this invention is illustrated in connection with a surgical procedure for securing a torn rotator cuff muscle to the humerus bone in the shoulder. The suture (5) is passed through a tunnel in the greater tuberosity of the humerus (B) and through the rotator cuff muscle (M) through holes formed in such body parts through a small diameter body opening or puncture wound, indicated by the letter (W). If desired, the small diameter wound (W) may be lined by the insertion of a tubular guide or cannula (6) (FIG. 6). The suture ends (5a) and (5b) extend outwardly through the wound (W) so that a first knot (K1) may be tied in such ends and displaced inwardly adjacent the exit of the suture from the body part by the knot pusher (10) heretofore described. The first formed knot preferably lies adjacent to the surface of bone (B) and it is difficult to effect a tight securement of any knot adjacent a bone surface by applying a tensile force on the knot which is generally perpendicular to the bone surface. The knot pusher (10) embodying this invention permits the application of tension forces (T) (shown in FIG. 6) to any knot being formed which are generally radial to the axis of the puncture wound (W) or the coaxial axis of the knot pusher (10). This is effected by the threading of the suture ends (5a) and (5b) through the suture guide notches (16) or channels ('16) formed in the perimeter of radial end face (14) of the knot pusher (10).

Referring back to FIG. 5, after the first knot (K1) has been formed, the suture knot clamping instrument (20) is inserted in the incision through the elongated slot (12) provided in the knot pusher (10) and the movable jaw (24) of the knot clamping instrument (20) is actuated to engage and clamp the first formed knot (K1). The suture ends disposed exteriorly of the body are then utilized to form a second knot (K2) and the knot pusher (10) is employed to push the second knot (K2) into close proximity to the first knot (K1) held between the clamping jaws (24) and (25) of the knot clamping instrument (20), as illustrated in enlarged scale in FIG. 6. Thus, the application of tensile force to both of the suture ends (5a) and (5b) which extend out of the body incision (I) will be translated into generally radially directed forces (T) at the location of the second knot (K2), permitting the second knot to be tightly formed adjacent the first knot (K1).

Obviously, any desired knot configuration which requires the application of radial forces to the portions of the suture forming the knot may be employed in addition to the common square knot illustrated in the drawings.

Referring to FIG. 7, a knot pusher (10') of the preferred embodiment has its entire cylindrical body of the same diameter which is slightly less than the diameter of the puncture wound or cannula into which the knot pusher (10') will be inserted. The inner end face (14,) may be flat or slightly concave to provide clearance for the prior throws of the knot. Suture guide channels (16') are provided extending from side wall through body and terminating near the periphery of concave inner face (14') in diametrically opposed relationship. A longitudinal slot (12') is provided to accommodate a knot clamping assembly (20). The operation of this embodiment is the same as that previously described.

Figure 8:
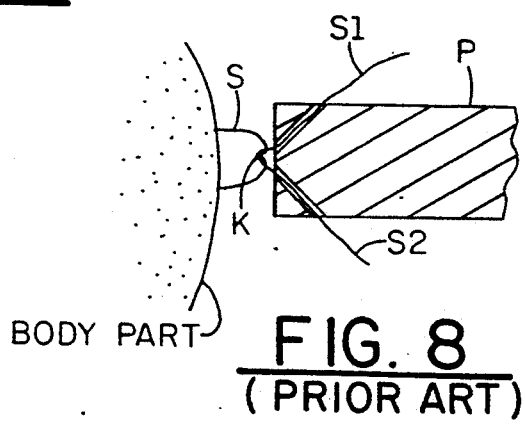
FIG. 8 is a schematic sectional view of a prior art knot pusher.

Referring to FIG. 8, there is shown a prior art knot pusher wherein the suture ends push through axially inclined holes in the inner face of the knot pusher (10). Such holes are closely spaced, hence are incapable of imparting sufficient radial tying forces to the suture knot.

It will be readily apparent to those skilled in the art that the method and apparatus of this invention permits the tying of suture knots in a remote location through an endoscopic surgical procedure with greater security than has heretofore been possible. One or a plurality of such knots may be formed. If a plurality of knots are to be formed, the knot grasping instrument (20) forming a part of the apparatus of this invention is employed to secure the previously tied knot or knots until the next knot is pushed into proximity therewith by the knot pusher (10) and tightened through the application of radial forces to the portions of the suture (5) adjacent the knot requiring tightening. Obviously, the method and apparatus of this invention may be employed in endoscopic surgery performed on any part of a human or animal body.

Modifications of this invention which would be obvious to those skilled in the art are intended to be included within the scope of the appended claims.

Further objects and advantages of the invention will be readily apparent to those skilled in the art from the following detailed description, taken in conjunction with the annexed sheets of drawings, on which is shown two preferred embodiments.

Terms such as "left", "right", "up", "down", "bottom", "top", "front", "back", "in", "out" and the like are applicable to the embodiment shown and described in conjunction with the drawings. These terms are merely for the purposes of description and do not necessarily apply to the position or manner in which the invention may be constructed or used.

What is claimed and desired to be secured by Letters Patent is:

1. A remote knot tier for the ends of a suture traversing a body part accessible by a puncture wound, the suture having ends extending outwardly through the puncture wound, comprising:

an elongated cylindrical knot pusher insertable within the puncture wound;

said knot pusher having a circular end face substantially perpendicular to the longitudinal axis of the knot pusher and engageable with a knot formed in said suture ends exteriorly of the body to move said knot through the puncture wound to its desired position adjacent the body part;

wherein said knot pusher defines a longitudinally extending recess extending substantially he full length of said knot pusher, and said knot pusher end face is slightly concave;

said circular end face of said knot pusher having opposed suture guides formed in said end face through which said suture ends pass, whereby application of a tensile force to said suture ends produces a knot tightening force in a plane parallel to said end face;

a knot holder having an elongated body portion insertable in said recess;

said body portion having a proximal and distal end;

a fixed jaw on the proximal end of said knot holder;

a movable jaw shiftably mounted on the proximal end of said knot holder cooperable with said fixed jaw to clamp a suture knot formed adjacent the body part; and means on the distal end of said knot holder for applying a force to said movable jaw to shift said movable jaw into a knot clamping position relative to said fixed jaw.

2. The apparatus of claim 1 wherein said fixed jaw and said movable jaw each have a planar clamping surface with the outermost edge of each clamping surface having a rounded contour at each end, whereby the next knot inserted by said knot pusher will be positioned snugly adjacent the knot clamped between said fixed and movable jaws.

3. The apparatus of claim 1 wherein the means for applying a force to said movable jaw comprises:
- a scissor handle pivotally mounted on the distal end of said body portion; and
- linkage means interconnecting said scissor handle to said movable jaw.

4. The method of tying the ends of a suture traversing body parts at an internal location accessible by a puncture wound comprising the steps of:
- bringing both ends of the suture out of the puncture wound;
- tying the suture ends in a first knot;
- pushing said first knot into a desired position relative to the body parts;
- clamping said first knot by a clamping tool inserted through the puncture wound;
- providing a cylindrical knot pusher having a longitudinal recess receiving said clamping tool and a radial end face having opposed suture guides proximate its periphery;
- forming a second knot in the suture ends;
- applying a tensile force to the suture ends to effect the application of opposed tensile forces to said second knot in a direction parallel to the body part surface; and
- moving the second knot towards the body parts by the end face of the knot pusher with the suture ends respectively disposed in said guide notches until the second knot reaches the surface of the body parts.

5. The method of claim 4 further comprising:
- forming a third knot in the suture ends;
- applying a tensile force to the suture ends to effect the application of opposed tensile forces to said third knot in a direction parallel to the body part surface; and
- moving the third knot inwardly by the end face of the knot pusher with the suture ends respectively disposed in said guide notches until the second knot reaches the surface of the body parts.

* * * * *